US00PP11383P

United States Patent [19]

Walden

[11] Patent Number: Plant 11,383

[45] Date of Patent: May 16, 2000

[54] MINIATURE ROSE PLANT NAMED 'JACQUEST'

[75] Inventor: John K. Walden, Thousand Oaks, Calif.

[73] Assignee: Bear Creek Gardens, Inc., Medford, Oreg.

[21] Appl. No.: 09/123,182

[22] Filed: Jul. 27, 1998

[51] Int. Cl.[7] ..... A01H 5/00

[52] U.S. Cl. ..... Plt./122

[58] Field of Search ..... Plt./122, 129

[56] References Cited

U.S. PATENT DOCUMENTS

P.P. 5,770 7/1986 De Ruiter ..... Plt./122

P.P. 6,054 12/1987 Laver ..... Plt./122

OTHER PUBLICATIONS

UPOV–ROM, 1999/02, Plant Variety Database, GTI Jouve Retrieval Software, citation for 'Jacquest'.

*Primary Examiner*—Howard J. Locker

*Attorney, Agent, or Firm*—Klarquist Sparkman Campbell Leigh & Whinston, LLP

[57] ABSTRACT

A miniature rose plant having bright red, 1½" flowers borne singly and in small cluster; high petal substance; upright pot rose habit; and long flower life.

1 Drawing Sheet

The present invention relates to a new and distinct variety of rose plant of the miniature class which was originated by me by crossing an unnamed seedling (whose parents are unnamed seedling×'RUImired' U.S. Plant Pat. No. 5,770), with the variety 'POULvic', U.S. Plant Pat. No. 8,012.

The primary objective of this breeding was to produce a new pot rose variety having red flowers with high petal substance (texture), flowers borne in small clusters, an upright plant habit suitable for potted plant production from softwood cuttings, grown in a greenhouse in 4-inch pots and possessing long flower life. The objective was substantially achieved, along with other desirable improvements, as evidenced by the following unique combination of characteristics that are outstanding in the new variety and that distinguish it from its parents, as well as from all other varieties of which I am aware:

1. Bright red, 1½ inch flowers, borne singly and in small clusters;
2. High petal substance;
3. Upright, pot rose habit; and
4. Long flower life (16 days).

The plant gives 18–21 days of shelf life, making it very suitable for use as a pot rose.

Asexual reproduction of this new variety by cuttings, as performed at Somis, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—Unnamed seedling. (unnamed seedling× 'RUImired' U.S. Plant Pat. No. 5,770.

*Pollen parent.*—'POULvic' (U.S. Plant Pat. No. 8,012).

Classification:

*Botanical.*—*Rosa hybrida.*

*Commercial.*—Miniature rose.

FLOWER

Observations made January 1995 to July 1998, from specimens grown in a greenhouse environment at Somis, Calif.

Blooming habit: Recurrent.

Bud:

*Size.*—About 11/16 inch long when the petals start to unfurl.

*Form.*—The bud form is pointed ovoid.

*Color.*—When sepals first divide, bud color is Red Group 46A. When half blown, the upper sides of the petals are Red Group 46B, and the lower sides of the petals are Red Group 45A.

*Sepals.*—Color: Near Yellow-Green Group 144A. Surface texture: Rough, with small glands. There are three heavily appendaged sepals. There are two unappendaged sepals with hairy edges.

*Receptacles.*—Color: Yellow-Green Group 144A. Shape: Funnel. Size: Small (about ⅛"×⅛"). Surface: Smooth.

*Peduncle.*—Length: Average about ¾". Surface: Rough, glandular. Color: Yellow-Green Group 144B. Strength: Stiff, erect.

Bloom:

*Size.*—Small. Average open size is 1½ inches.

*Borne.*—Singly and several together in rounded clusters of three to nine blooms.

*Stems.*—Normal. Average length is about 5 to 5¼ inches.

*Form.*—When first open: High centered. Permanence: Outer petal edges curl slightly.

*Petalage.*—Number of petals under normal conditions: 25–30.

*Color.*—The upper sides of the petals are Red Group 45B. The reverse sides of the petals are Red Group 46D. The base of each petal has a small white spot at the point of attachment. The major color on the upper sides is Red Group 45B.

*Variegations.*—None.

*Discoloration.*—At the end of the first day: Red Group 46B. At the end of the third day: Red Group 46B. Thereafter deepens toward Red Group 46A.

*Fragrance.*—None.

Petals:

*Texture.*—Thick, leathery.

*Shape.*—Oval.

*Form.*—Tips quilled to a point.

*Arrangement.*—Imbricated; shingle-like. Petaloids in the center are few to none.

*Persistence.*—Petals drop off cleanly before drying.

*Lastingness.*—On the plant: Very long (16+ days). As a cut flower: Not tested.

Reproductive parts:

*Anthers.*—Size: Medium. Quantity: Many. Color: Yellow-Orange Group 15B. Arrangement: Regular around styles.

*Filaments.*—Color: Yellow at base, reddish at top.

*Pollen.*—Color: Yellow-Orange Group 15B.

*Styles.*—Color: Greenish at base, reddish at top half.

*Stigmas.*—Color: Green-White Group 151D.

Plant:

*Form.*—Bush.

*Growth.*—Vigorous, dwarf, upright.

*Mature plant.*—Height: 12–14 inches. Width: 12–14 inches.

Foliage: Number of leaflets — on normal mid-stem leaves: Five.

*Size.*—Small, (about 2¼ inches long×1⅜ inches wide).

*Quantity.*—Normal.

*Color.*—New foliage: Upper and lower surfaces: Red-Purple Group 59B, changing rapidly to green. Old foliage: Upper surface: Near Green Group 137A. Lower surface: Green Group 147B.

*Shape.*—Broadly oval.

*Texture.*—Upper side: Matte, smooth.

*Edge.*—Serrated.

*Serration.*—Single.

*Petiole rachis.*—Color: Green Group 141C.

*Petiole underside.*—With prickles.

*Stipules.*—Short (about 5/16" long), serrated.

*Disease resistance.*—Resistant to mildew under normal growing conditions at Somis, Calif. Not tested for blackspot.

Wood:

*New wood.*—Color: Yellow-Green Group 144A. Bark: Smooth.

*Old wood.*—Color: Yellow-Green Group 144A. Bark: Rough.

Prickles:

*Quantity.*—On main canes from base: Ordinary. On laterals from main canes: Ordinary.

*Form.*—Slightly hooked downward.

*Color when young.*—Greyed-Yellow Group 161D.

*Color when mature.*—Greyed-Brown Group 199A.

Small prickles:

*Quantity.*—On main stalks: None. On laterals: None.

I claim:

1. A novel rose plant of the miniature class as herein shown and described, characterized particularly as to novelty by its bright red, 1½" flowers borne singly and in small clusters; high petal substance; upright pot rose habit; and long flower life.

* * * * *

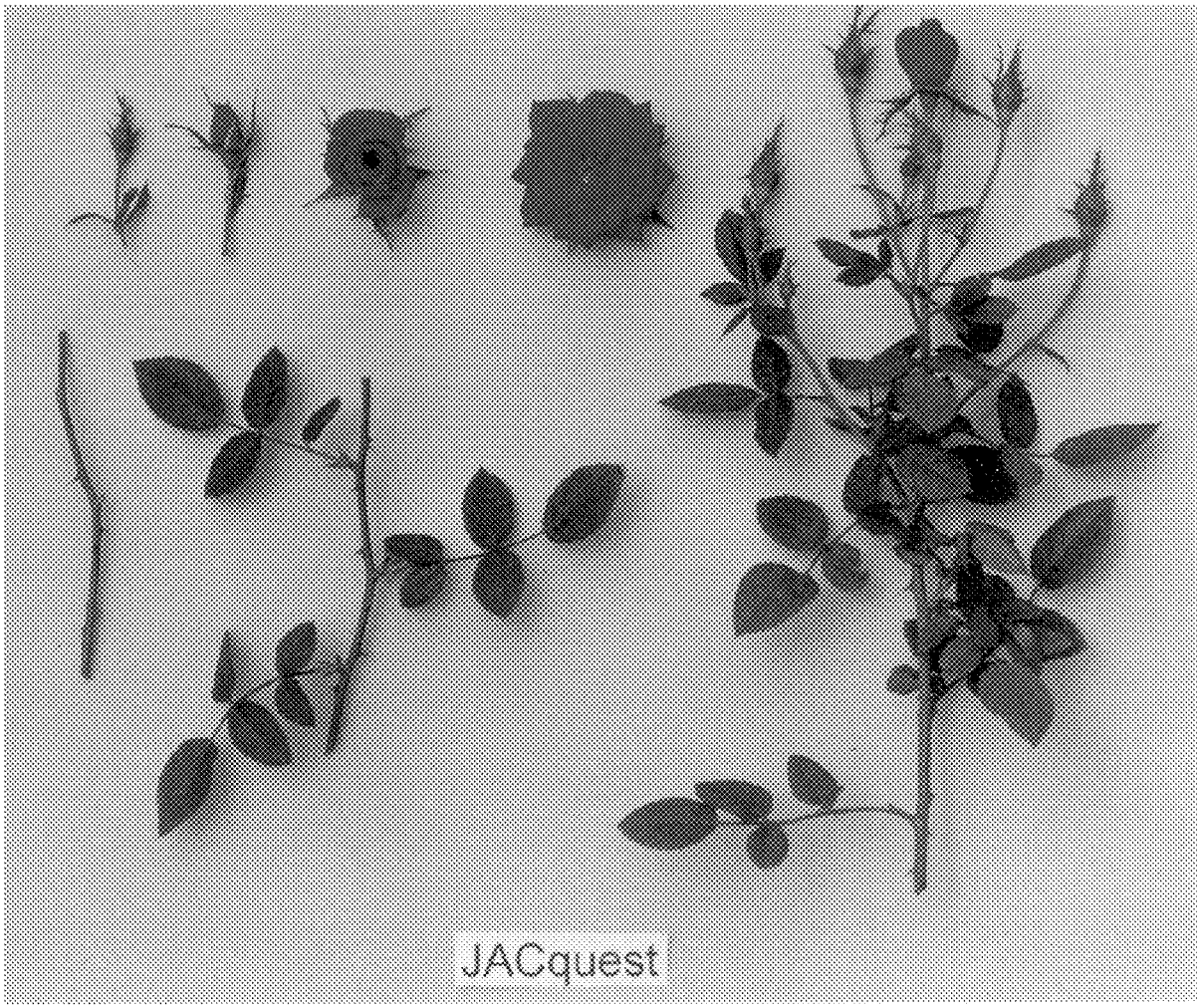
JACquest

UNITED STATES PATENT AND TRADEMARK OFFICE
CERTIFICATE OF CORRECTION

PATENT NO. : PP11,383

DATED : May 16, 2000

INVENTOR(S) : John K. Walden

It is certified that errors appear in the above-identified patent and that said Letters Patent is hereby corrected as shown below:

| Col./Line | Error Reads | Should Read |
|---|---|---|
| Abstract | cluster; | clusters; |
| 1/41 | seedling. (unnamed | seedling (unnamed |
| 1/42 | Pat. No. 5,770. | Pat. No. 5,770.) |

Signed and Sealed this

Twenty-ninth Day of May, 2001

*Attest:*

Nicholas P. Godici

NICHOLAS P. GODICI

*Attesting Officer*

*Acting Director of the United States Patent and Trademark Office*